US006287779B1

(12) United States Patent
Engel et al.

(10) Patent No.: US 6,287,779 B1
(45) Date of Patent: Sep. 11, 2001

(54) DETECTION OF FERMENTATION-RELATED MICROORGANISMS

(75) Inventors: Stacia R. Engel; Richard A. Morenzoni; Nancy A. Irelan, all of Modesto, CA (US)

(73) Assignee: E. & J. Gallo Winery, Modesto, CA (US)

( * ) Notice: Subject to any disclaimer, the term of this patent is extended or adjusted under 35 U.S.C. 154(b) by 0 days.

(21) Appl. No.: 09/488,295

(22) Filed: Jan. 20, 2000

(51) Int. Cl.$^7$ .............................. C12Q 1/68; C07H 21/04

(52) U.S. Cl. ................................. 435/6; 435/91.2; 435/5; 536/23.1; 536/24.3; 536/24.32

(58) Field of Search .................................. 435/6, 5, 91.2; 536/23.1, 24.3, 24.32

(56) References Cited

U.S. PATENT DOCUMENTS

| | | | |
|---|---|---|---|
| 4,230,625 | 10/1980 | Despreaux et al. | 260/397.1 |
| 4,301,246 | 11/1981 | Despreaux et al. | 435/58 |
| 4,683,195 | 7/1987 | Mullis et al. | 435/6 |
| 4,683,202 | 7/1987 | Mullis | 435/91 |
| 5,149,624 | 9/1992 | Gabriel | 435/6 |
| 5,389,513 | 2/1995 | Baquero et al. | 435/6 |
| 5,389,515 | 2/1995 | Chmelo et al. | 435/6 |
| 5,403,710 | 4/1995 | Weisburg et al. | 435/6 |
| 5,426,027 | 6/1995 | Lott et al. | 435/6 |
| 5,434,048 | 7/1995 | Simon et al. | 435/6 |
| 5,545,525 | 8/1996 | Montplaisir et al. | 435/6 |
| 5,580,971 | 12/1996 | Mitsuhashi | 536/24.32 |
| 5,585,238 | 12/1996 | Ligon et al. | 435/6 |
| 5,622,827 | 4/1997 | McAllister et al. | 435/6 |
| 5,627,275 | 5/1997 | Roll | 536/23.7 |
| 5,631,132 | 5/1997 | Lott et al. | 435/6 |
| 5,635,353 | 6/1997 | Lott et al. | 435/6 |
| 5,792,611 | 8/1998 | Hamelin | 435/6 |

FOREIGN PATENT DOCUMENTS

| | | |
|---|---|---|
| 2 781 812 | 4/2000 | (FR) . |
| WO 99/29899 | 6/1999 | (WO) . |
| WO 99/46405 | 9/1999 | (WO) . |

OTHER PUBLICATIONS

Ahern, www.thescientist.library.upenn.edu/yr1995/july/tools_950724.htlm, Dec. 22, 1998.*
GenBank Sequence Alignment Packet. No date.*
Van der Sande et al, "Functional Analysis of ITS2 of *Saccharomyces cerevisiae* Ribosomal DNA" J. Mol. Biol. vol. 223, No. 4, p. 899–910, 1992.*
Oda et al "Reexamination of Yeast strains classified as Torulaspora delbrueckii" Int. J. of Systematic Bacteriology, vol. 47, No. 4, p. 1102–1106, Oct. 1997.*
Goddard et al "Recurrent invasion and extinction of a selfish gene" PNAS, vol. 96, No. 24, p. 13880–13885, Nov. 1999.*

Van Nues et al "Separate structural elements within internal transcribed spacer 1 of *Saccharomyces cervisiae* precursor ribosomal RNA direct the formation of 17S and 26S rRNA" Nucleic Acids Research, vol. 22, No. 6, p. 912–919, 1994.*
Albert, H.H. et al., "PCR Amplification from a Homolog of the bE Mating–Type Gene as a Sensitive Assay for the Presence of *Ustilago scitaminea* DNA," *Plant Disease*, 80 (10):1189–1192 (1996).
Alm, E.W. et al., "The Oligonucleotide Probe Database," *Applied and Environmental Microbiology*, 62(10):3557–3559 (1996).
Appel, D.J. et al., "Relationship Among Pathogenic and Nonpathogenic Isolates of *Fursarium oxysporum* Based on the Partial Sequence of the Intergenic Spacer Region of the Ribosomal DNA," *MPMI*, 9(2):125–138 (1996).
Audy, P. et al., "A Rapid and Sensitive PCR–Based Assay for Concurrent Detection of Bacteria Causing Common and Halo Blights in Bean Seed," *Phytopathology*, 86(4):361–366 (1996).
Border, P.M. et al., "Detection of Listeria species and Listeria monocytogenes using polymerase chain reaction," *Letters in Applied Microbiology*, 11:158–162 (1990).
Boysen, M. et al., "Reclassification of the *Penicillium roqueforti* group into three species on the basis of molecular genetic and biochemical profiles," *Microbiology*, 142:541–549 (1996).
Carter, M.V. et al., "An annotated host list and bibliography of *Eutypa armeniacae*," *Review of Plant Pathology*, 62(7):251–258 (1983).
Casey, G.P. et al., "Evaluation of Recent Techniques Used to Identify Individual Strains to Saccharomyces Yeasts," *Journal of the American Society of Brewing Chemists*, 48(3):100–106 (1990).
Couto, M. et al., "Evaluation of Molecular Typing Techniques To Assign Genetic Diversity among *Saccharomyces cerevisiae* Strains," *Applied and Environmental Microbiology*, 62(1):41–46 (1996).
Couto, M.M., "Random amplified polymorphic DNA and restriction enzyme analysis of PCR amplified rDNA in taxonomy: two identification techniques for food–borne yeasts," *J. Appl. Bacteriol.*, 79(5):525–535 (1995).
Couto, M.M., "RAPD analysis: a rapid technique for differentiation of spoilage yeasts," *Int. J. Food Microbiol.*, 24(1–2):249–260 (1994).
Davies, D.L. et al., "Detection of Phytoplasmas Associated With Pear Decline In Pear Psyllids By Polymerase Chain Reaction,"In: *1996 BCPC Symposium Proceedings No. 65: Diagnostics in Crop Production*, pp. 67–72 (1996).

(List continued on next page.)

Primary Examiner—Lisa B. Arthur
Assistant Examiner—Jeanine Goldberg
(74) Attorney, Agent, or Firm—Marshall, O'Toole, Gerstein, Murray & Borun

(57) ABSTRACT

Unique DNA sequences characteristic of fermentation-related microorganisms are provided which are useful as primers in PCR-based analysis for identification of fermentation-related microorganisms

21 Claims, No Drawings

OTHER PUBLICATIONS

DeBarros Lopes, M. et al., "PCR Differentiation of Commercial Yeast Strains Using Intron Splice Site Primers," *Applied and Environmental Microbiology*, 62(12):4514–4520 (1996).

Degré, R. et al., "Wine Yeasts Strain Identification," *American Journal of Enology and Viticulture*, 40(4):309–315 (1989).

Di Bonita, R. et al., "Detection of an Arbuscular Mycorrhizal Fungus in Roots of Different Plant Species with the PCR," *Applied and Environmental Microbiology*, 61(7):2809–2810 (1995).

Doss, R.P. et al., "A Polymerase Chain Reaction–Based Procedure for Detection of *Acremonium coenophialum* in Tall Fescue," *Phytopathology*, 85(8):913–917 (1995).

Elie, C.M. et al., "Rapid Identification of Candida species with species–specific DNA probes," *J. Clin. Microbiol.*, 36(11):3260–3265 (1998).

Fell, J.W., "Rapid identification of yeast species using three primers in a polymerase chain reaction," *Molecular Marine Biology and Biotechnology*, 2(3):174–180 (1993).

Fell, J.W., "rDNA targeted oligonucleotide primers for the identification of pathogenic yeasts in a polymerase chain reaction," *Journal of Industrial Microbiology*, 14(6):475–477 (1995).

Gardes, M. et al., In: *Methods in Molecular Biology, vol. 50:Species Diagnostics Protocols: PCR and Other Nucleic Acid Methods*, Ed. J.P. Clapp, Humana Press, Inc, Totowa, NJ, pp. 177–186 (1996).

Gardes, M. et al., "ITS primers with enhanced specificity for basidiomycetes—application to the identification of mycorrhizae and rusts," *Molecular Ecology*, 2:113–118 (1993).

GenBank Accession No. AB011507, "*Kluyveromyces nonfermentans* genes for 18S rRNA, partial and complete sequence," Nagahama, T. et al., submitted Feb. 1998.

GenBank Accession No. AB011508, "*Kluyveromyces nonfermentans* genes for 18S rRNA, 5.8S rRNA, partial and complete sequence," Nagahama, T. et al., submitted Feb. 1998.

GenBank Accession No. AB011509, "*Kluyveromyces nonfermentans* genes for 18S rRNA, 5.8S rRNA, partial and complete sequence," Nagahama, T. et al., submitted Feb. 1998.

GenBank Accession No. AB011510, "*Kluyveromyces nonfermentans* genes for 18S rRNA, 5.8S rRNA, partial and complete sequence," Nagahama, T. et al., submitted Feb. 1998.

GenBank Accession No. AB011511, "*Kluyveromyces nonfermentati* gene for 5.8S rRNA, complete sequence," Nagahama, T. et al., Feb. 1998.

GenBank Accession No. AB011512, "*Kluyveromyces nonfermentans* gene for 5.8S rRNA, complete sequence," Nagahama, T. et al., submitted Feb. 1998.

GenBank Accession No. AB011513, "*Kluyveromyces aestuarii* gene for 5.8S rRNA, complete sequence," Nagahama, T. et al., submitted Feb. 1998.

GenBank Accession No. AB011514, "*Kluyveromyces dobzhanskii* 5.8S rRNA, complete sequence," Nagahama, T. et al., submitted Feb. 1998.

GenBank Accession No. AB011515, "*Kluyveromyces lactis* gene for 5.8S rRNA, complete sequence," Nagahama, T. et al., submitted Feb. 1998.

GenBank Accession No. AB011516, "*Kluyveromyces lactis* gene for 5.8S rRNA, complete sequence," Nagahama, T. et al., submitted Feb. 1998.

GenBank Accession No. AB011517, "*Kluyveromyces lactis* gene for 5.8S rRNA, complete sequence," Nagahama, T. et al., submitted Feb. 1998.

GenBank Accession No. AB011518, "*Kluyveromyces marianus* gene for 5.8S rRNA, complete sequence," Nagahama, T. et al., submitted Feb. 1998.

GenBank Accession No. AB011519, "*Kluyveromyces marxianus* gene for 5.8S rRNA, complete sequence," Nagahama, T. et al., submitted Feb. 1998.

GenBank Accession No. AB011520, "*Kluyveromyces marxianus* gene for 5.8S rRNA, complete sequence," Nagahama, T. et al., submitted Feb. 1998.

GenBank Accession No. AB011521, "*Kluyveromyces wickerhamii* gene for 5.8S rRNA, complete sequence," Nagahama, T. et al., submitted Feb. 1998.

GenBank Accession No. AB012264, "*Kluyveromyces nonfermentans* genes for 18S rRNA, 5.8S rRNA, partial and complete sequence," Nagahama, T. et al., submitted Mar. 1998.

GenBank Accession No. AF033472, "*Penicillium crustosum* strain NRRL 968 internal transcribed spacer 1, 5.8S ribosomal RNA gene and internal transcribed spacer 2, complete sequence; and 28S ribosomal RNA gene, partial sequence," Peterson, S.W., submitted Nov. 1997.

GenBank Accession No. AF034453, "*Penicillium camemberti* internal transcribed spacer 1, 5.8S ribosomal RNA gene and internal transcribed spacer 2, complete sequence, and 28S ribosomal RNA gene, partial sequence," Peterson, S.W., submited Nov. 1997.

GenBank Accession No. AF121136, "*Debaryomyces polymorphus* internal transcribed spacer 1, partial sequence; 5.8S ribosomal RNA gene, complete sequence; and internal transcribed spacer 2, partial sequence," Ramos, J.P. et al., submitted Jan. 1999.

GenBank Accession No. AJ229066, "*Torulaspora pretoriensis* 5.8S gene and ITS1 and ITS2 (strain CBS 5080)," Goddard, M.R. submitted May 1998.

GenBank Accession No. AJ229067, "*Zygosaccharomyces bailii* DNA for ITS1 (strain CBS 685)," Goddard, M.R., submitted May 1998.

GenBank Accession No. AJ229068, "*Kluyveromyces dobzhanskii* 5.8S gene and ITS1 and ITS2 (strain CBS 2104)," Goddard, M.R., submitted May 1998.

GenBank Accession No. AJ229069, "*Kluyveromyces lactis* 5.8S gene and ITS1 and ITS2 (strain CBS 683)," Goddard, M.R., submitted May 1998.

GenBank Accession No. AJ229070, "*Zygosaccharomyces bailii* DNA for ITS2 (strain CBS 685)," Goddard, M.R., submitted May 1998.

GenBank Accession No. AJ229071, "*Zygosaccharomyces rouxii* 5.8S gene and ITS1 and ITS2 (strain CBS 688)," Goddard, M.R., submitted May 1998.

GenBank Accession No. AJ229073, "*Kluyveromyces thermotolerans* 5.8S gene and ITS1 and ITS2 (strain CBS 6924)," Goddard, M.R., submitted May 1998.

GenBank Accession No. AJ229074, "*Torulaspora globosa* 5.8S gene and ITS1 and ITS2 (strain CBS 764)," Goddard, M.R. submitted May 1998.

GenBank Accession No. AJ229075, "*Torulaspora delbrueckii* 5.8S gene and ITS1 and ITS2 (strain CBS 404)," Goddard, M.R., submitted May 1998.

GenBank Accession No. AJ229076, "*Kluyveromyces polysporus* 5.8S gene and ITS1 and ITS2 (strain CBS 2163)," Goddard, M.R., submitted May 1998.
GenBank Accession No. AJ229176, "*Zygosaccharomyces bisporus* 5.8S gene and ITS1 and ITS2 (strain CBS 702)," Goddard, M.R., submitted May 1998.
GenBank Accession No. B00803, "cSRL–11f4–u cSRL flow sorted Chromosome 11 specific cosmid *Home sapiens* genomic clone cSRL–11f4," Evans, G.A. et al. (1996).
GenBank Accession No. B04605, "cSRL–32d2–u cSRL flow sorted Chromosome 11 specific cosmid *Homo sapiens* genomic clone cSRL–39d2," Evans, G.A. et al. (1996).
GenBank Accession No. D89598, "*Torulaspora delbrueckii* gene for 18S rRNA, 5.8S rRNA and 28S rRNA, partial and complete sequence," Fukunaga, M., submitted Nov. 1996.
GenBank Accession No. D89599, "*Torulaspora delbrueckii* gene for 18S rRNA, 5.8S rRNA and 28S rRNA, partial and complete sequence," Fukunaga, M., submitted Nov. 1996.
GenBank Accession No. D89600, "*Torulaspora delbrueckii* gene for 18S rRNA, 5.8S rRNA and 28S rRNA, partial and complete sequence," Fukunaga, M., submitted Nov. 1996.
GenBank Accession No. D89601, "*Torulaspora delbrueckii* gene for 18S rRNA, 5.8S rRNA and 28S rRNA, partial and complete sequence," Fukunaga, M., submitted Nov. 1996.
GenBank Accession No. D89602, "*Torulaspora delbrueckii* gene for 18S rRNA, 5.8S rRNA and 28S rRNA, partial and complete sequence," Fukunaga, M., submitted Nov. 1996.
GenBank Accession No. D89603, "*Torulaspora delbrueckii* gene for 18S rRNA, 5.8S rRNA and 28S rRNA, partial and complete sequence," Fukunaga, M., submitted Nov. 1996.
GenBank Accession No. D89604, "*Torulaspora delbrueckii* gene for 18S rRNA, 5.8S rRNA and 28S rRNA, partial and complete sequence," Fukunaga, M., submitted Nov. 1996.
GenBank Accession No. D89605, "*Torulaspora delbrueckii* gene for 18S rRNA, 5.8S rRNA and 28S rRNA, partial and complete sequence," Fukunaga, M., submitted Nov. 1996.
GenBank Accession No. D89886, "*Saccharomyces cerevisiae* gene for 18S rRNA, 5.8S rRNA and 28S rRNA, partial and complete sequence," Fukunaga, M., submitted Dec. 1996.
GenBank Accession No. L11350, "*Candida krusei* 5.8S ribosomal RNA gene," Lott, T.J. et al., submitted Mar. 1993.
GenBank Accession No. L47107, "*Kluyveromyces marxianus* 18S ribosomal RNA gene, 3' end, 5.8S ribosomal RNA gene, complete sequence, 25S ribosomal RNA gene, 5' end," Williams, D., submitted Sep. 1995.
GenBank Accession No. L47113, "*Candida krusei* 18S ribosomal RNA gene, 3' end, 5.8S ribosomal RNA gene, complete, 25S ribosomal RNA gene, 5' end," Williams, D.W., (1995).
GenBank Accession No. L47116, *Candida krusei* 18S ribosomal RNA gene, 3' end, 5.8S ribosomal RNA gene, complete, 25S ribosomal RNA gene, 5' end, Williams, D.W. (1995).
GenBank Accession No. U09324, "*Kluyveromyces aestuarii* strain NRRL Y–4510 internal transcribed spacer 1 (ITS) and 2 (ITS2) and 5.8S rRNA gene, complete sequence," Messner, R., submitted Apr. 1994.
GenBank Accession No. U09325, "*Kluyveromyces marxianus* strain HA38 internal transcribed spacer 1 (ITS) and 2 (ITS2) and 5.8S rRNA gene, complete sequence," Messner, R., submitted Apr. 1994.

GenBank Accession No. U09327, "*Saccharomyces cerevisiae* strain HA6 internal transcribed spacer 1 (ITS1) and 2 (ITS2) and 5.8S rRNA gene, complete sequence," Messner, R. et al., submitted Apr. 1994.
GenBank Accession No. U51433, "*Metschnikowia zobellii* 5.8S ribosomal RNA gene and internal transcriber spacers 1 and 2, complete sequence," Schweigkofler, W., submitted Mar. 1996.
GenBank Accession No. U51434, "*Metschnikowia hawaiiensis* 5.8S ribosomal RNA gene and internal transcribed spacers 1 and 2, complete sequence," Scheweigkofler, W., submitted Mar. 1996.
GenBank Accession No. U51436, "*Metschnikowia bicuspidata* 5.8S ribosomal RNA gene and internal transcribed spacers 1 and 2, complete sequence," Scheweigkofler, W., submitted Mar. 1996.
GenBank Accession No. U70500, "*Debaryomyces hasenii* internal transcribed spacer 2 (ITS) gene," Lott, T.J. et al., submitted Sep. 1996.
GenBank Accession No. U70502, "*Kluyveromyces marxianus* internal transcribed spacer 2 (ITS2) gene," Lott, T.J. et al., submitted Sep. 1996.
GenBank Accession No. U96720, "*Pichia anomala* ATCC 8168 rDNA internal transcriber spacer 2," Lott, T.J., submitted Apr. 1997.
GenBank Accession No. X64951, "*T. delbrueckii* gene for 5.8S and 26S ribosomal RNA," Van Nues, R.W., submitted Jul. 1994.
GenBank Accession No. X80274, "*K. lactis* 5.8S–ITS2 rDNA," Van Nues, R.W., submitted Jul. 1994.
GenBank Accession No. X80275, "*T. delbrueckii* internal transcribed spacer 2 from rDNA," Van Nues, R.W., submitted Jul. 1994.
GenBank Accession No. X80672, "*K. marxianus* 5.8S–ITS2 rDNA," Van Nues, R.W., submitted Jul. 1994.
GenBank Accession No. X82361, "*P. crustosum* 5.8S rRNA gene," Boysen, M. et al., submitted Oct. 1994.
GenBank Accession No. X84640, "*Z. bailii* rRNA ITS1 spacer region DNA," James, S.A., submitted Feb. 1995.
GenBank Accession No. X84641, "*Z. bailii* rRNA ITS2 spacer region DNA, " James, S.A., submitted Feb. 1995.
GenBank Accession No. X84642, "*Z. bisporus* rRNA ITS1 spacer region DNA," James, S.A., submitted Feb. 1995.
GenBank Accession No. X84643, "*Z. bisporus* rRNA ITS2 spacer region DNA," James, S.A., submitted Feb. 1995.
GenBank Accession No. X84644, "*Z. rouxii* rRNA ITS1 spacer region DNA," James, S.A., submitted Feb. 1995.
GenBank Accession No. X84645, "*Z. rouxii* rRNA ITS spacer region DNA," James, S.A., submitted Feb. 1995.
GenBank Accession No. X84732NID, "*Z. bailii* rDNA ITS 1 spacer," James, S.A., submitted Feb. 1995.
GenBank Accession No. X84733, "*Z. bailii* rDNA ITS 2 spacer," James, S.A., submitted Feb. 1995.
GenBank Accession No. X87129, "*Z. bailii* internal transcribed spacer 1 DNA," James, S.A., submitted May 1995.
GenBank Accession No. X87130, "*Z. bailii* internal transcribed spacer 2 DNA," James, S.A., submitted May 1995.
GenBank Accession No. Y16815, "*Zygosaccharomyces lentus* internal transcribed spacer 1, strain NCYC 2789," James, S.A., submitted Mar. 1998.
GenBank Accession No. Y16816, "*Zygosaccharomyces lentus* internal transcribed spacer 2, strain NCYC 2789," James, S.A., submitted Mar. 1998.

GenBank Accession No. Y16817, "*Zygosaccharomyces lentus* internal transcribed spacer 1, strain NCYC 2406," James, S.A., submitted Mar. 1998.

GenBank Accession No. Z29384, "*K. lactis* ribosomal RNA and internal transcribed spacer 2," Nues, R.W., submitted Jan. 1994.

GenBank Accession No. Z29385, "*K. marxianus* ribosomal RNA and internal transcribed spacer 1," Nues, R.W., submitted Jan. 1994.

GenBank Accession No. Z29483, "*T. delbrueckii* (*S. rosei*) ribosomal RNA and internal transcribed spacer 1," Nues, R.W., submitted Jan. 1994.

GenBank Accession No. Z48309, "*T. delbrueckii* DNA for internal transcribed spacer 1," James, S.A., submitted Feb. 1995.

GenBank Accession No. Z48310, "*T. delbrueckii* DNA for internal transcribed spacer 1," James, S.A., submitted Feb. 1995.

GenBank Accession No. Z48311, "*T. delbrueckii* DNA for internal transcribed spacer 2," James, S.A., submitted Feb. 1995.

GenBank Accession No. Z48312, "*T. pretoriensis* DNA for internal transcribed spacer 2," James, S.A., submitted Feb. 1995.

GenBank Accession No. Z48335, "*T. globosa* DNA for internal transcribed spacer 1," James, S.A., submitted Feb. 1995.

GenBank Accession No. Z48336, "*T. globosa* DNA for internal transcribed spacer 2," James, S.A., submitted Feb. 1995.

GenBank Accession No. Z48347, "*Z. cidri* DNA for internal transcribed spacer 1," James, S.A., submitted Feb. 1995.

GenBank Accession No. Z48348, "*Z. florentinus* DNA for internal transcribed spacer 1," James, S.A., submitted Feb. 1995.

GenBank Accession No. Z48349, "*Z. mellis* DNA for internal transcribed spacer 1," James, S.A., submitted Feb. 1995.

GenBank Accession No. Z48350, "*Z. microellipsoides* DNA for internal transcribed spacer 1," James, S.A., submitted Feb. 1995.

GenBank Accession No. Z48351, "*Z. mrakii* DNA for internal transcribed spacer 1," James, S.A., submitted Feb. 1995.

GenBank Accession No. Z48358, "Z. fermentati DNA for internal transcribed spacer 1," James, S.A., submitted Feb. 1995.

GenBank Accession No. Z48361, "*Z. cidri* DNA for internal transcribed spacer 2," James, S.A., submitted Feb. 1995.

GenBank Accession No. Z48362, "*Z. fermentati* DNA for internal transcribed spacer 2," James, S.A., submitted Feb. 1995.

GenBank Accession No. Z48363, "*Z. florentinus* DNA for internal transcribed spacer 2," James, S.A., submitted Feb. 1995.

GenBank Accession No. Z48364 "*Z. mellis* DNA for internal transcribed spacer 2," James, S.A., submitted Feb. 1995.

GenBank Accession No. Z48365, "*Z. microellipsoides* DNA for internal transcribed spacer 2," James, S.A., submitted Feb. 1995.

GenBank Accession No. Z48366, "*Z. mrakii* DNA for internal transcribed spacer 2," James, S.A., submitted Feb. 1995.

GenBank Accession No. Z73765 (Locus BCINEITSB), "*B. cinerea* gene for 5.8S ribosomal RNA, internal transcribed spacer 1 and internal transcribed spacer 2," Holst–Jensen, A. et al., submitted May, 1996.

Glass, N.L. et al., "Development of Primer Sets Designed for Use with the PCR To Amplify Conserved Genes from Filamentous Ascomycetes," *Applied and Environmental Microbiology*, 61(4):1323–1330 (1995).

Graham, T. et al., "Genus– and species–specific detection of *Listeria monocytogenes* using polymerase chain reaction assays targeting the 16S/23S intergenic spacer region of the rRNA operon," *Can. J. Microbiol.*, 42:1155–1162 (1996).

Guillamón, J.M. et al., "Characterization of Wine Yeast Strains of the Saccharomyces Genus on the Basis of Molecular Markers: Relationships Between Genetic Distance and Geographic or Ecological Origin," *Systematic and Applied Microbiology*, 19:122–132 (1996).

Guillamon, J.M. et al., "Rapid identification of wine yeast species based on RFLP analysis of the ribosomal internal transcribed spacer (ITS) region," *Arch. Microbiol.*, 169:387–392 (1998).

Hamelin, R.C. et al., "Identification of Root Rot Fungi in Nursery Seedlings by Nested Multiplex PCR," *Applied and Environmental Microbiology*, 62(11):4026–4031(1996).

Haynes, K.A. "Rapid identification of *Candida albicans, C. glabrata, C. parapsilosis* and *C. krusei* by species–specific PCR of large subunit ribosomal DNA," *J. Med. Microbiol.*, 44:390–396 (1996).

Hoeben, P. et al., "An approach to yeast classification by mapping mitochondrial DNA from Dekkera/Brettanomyces and Eeniella genera," *Current Genetics*, 10:371–379 (1986).

Holst–Jensen, A. et al., "Molecular Phylogeny and Evolution of Monilinia (Sclerotiniaceae) Based on Coding and Noncoding rDNA Sequences," *American J. Botany*, 84(5):686–701 (1997).

Ibeas, J.I., "Detection of Dekkera–Brettanomyces Strains in Sherry by a Nested PCR Method," *Applied and Environmental Microbiology*, 62(3):998–1003 (1996).

IntelliGenetics, FastDB –Fast Pairwise Comparison of Sequences Release 5.4, Results file af033472.res made by schreib.

IntelliGenetics, FastDB –Fast Pairwise Comparison of Sequences Release 5.4, Results file d89886.res made by schreib.

IntelliGenetics, FastDB –Fast Pairwise Comparison of Sequences Release 5.4, Results file 147113.res made by schreib.

IntelliGenetics, FastDB –Fast Pairwise Comparison of Sequences Release 5.4, Results file af034453.res made by schreib.

IntelliGenetics, FastDB –Fast Pairwise Comparison of Sequences Release 5.4, Results file u09327.res made by schreib.

IntelliGenetics, FastDB –Fast Pairwise Comparison of Sequences Release 5.4, Results file x82361.res made by schreib.

James, S.A. et al., "Use of an rRNA internal transcribed spacer region to distinguish phylogenetically closely related species of the genera Zygosaccharomyces and Torulaspora," *Int. J. Syst. Bacteriol.*, 46(1):189–194 (1996).

Kong, R.Y.C. et al., "Co–detection of Three Species of Water–Borne Bacteria by Multiplex PCR," *Marine Pollution Bulletin*, 31(4–12):317–324 (1995).

Kricka, L.J., "Prospects for chemiluminescent and bioluminescent immunoassay and nucleic acid assays in food testing and the pharmaceutical industry," *J. Biolumin. Chemilumin.*, 13(4):189–193 (1998).

Kumeda, Y. et al. "Single–Stranded Conformation Polymorphism Analysis of PCR–Amplified Ribosomal DNA Internal Transcribed Spacers to Differentiate Species of Aspergillus Section Flavi," *Applied and Environmental Microbiology*, 62(8):2947–2952 (1996).

Lavalleé, F. et al., "PCR and DNA Fingerprinting Used as Quality Control in the Production of Wine Yeast Strains," *American Journal of Enology and Viticulture*, 45(1):86–91 (1994).

Lee, S.B. et al., *Fungal Genetics Newsletter*, No. 35, pp. 23–24 (1988).

Lee, S.B. et al., "Isolation of DNA from Fungal Mycelia and Single Spores," In: *PCR Protocols: A Guide to Methods and Applications*, Innes et al. (Eds.), Academic Press, Inc., pp. 282–287 (1990).

Li, K. et al., "PCR Primers That Allow Intergeneric Differentiation of Ascomycetes and Their Application to Verticillium spp.," *Applied and Environmental Microbiology*, 60(12):4324–4331 (1994).

Lieckfeldt, E. et al., "Rapid identification and differentiation of yeasts by DNA and PCR fingerprinting," *Journal of Basic Microbiology*, 33(6):413–425 (1993).

Lott, T.J. et al., "Nucleotide sequence analysis of the 5.8S rDNA and adjacent ITS2 region of *Candida albicans* and related species," *Yeast*, 9(11):1199–1206 (1993).

Lott, T.J. et al., "Sequence analysis of the internal transcribed spacer 2 (ITS) from yeast species within the genus Candida," *Curr. Microbiol.*, 36(2):63–69 (1998).

Maiwald, M. et al., "Rapid presumptive identification of medically relevant yeasts to the species level by polymerase chain reaction and restriction enzyme analysis," *J. Medical and Veterinary Mycology*, 32:115–122 (1994).

Manavathu, E.K. et al., "Isolation and characterization of a species–specific DNA probe for the detection of *Candida krusei*," Curr. Microbio., 33:147–151 (1996).

Mazzola, M. et al., "Virulence of *Rhizoctonia oryzae* and *R. solani* AG–8 on Wheat and Detection of *R. oryzae* in Plant Tissue by PCR," *Phytopathology*, 86(4):354–360 (1996).

Možina, S.S. et al., "Identification of *Saccharomyces sensu stricto* and Torulaspora yeasts by PCR ribotyping," *Letters in Applied Microbiology*, 24(4):311–315 (1997).

Muncan, P. et al., "Early Identification of Candiduria By Polymerase Chain Reaction in High Risk Patients," *J. Urology*, 156:154–156 (1996).

Nakagawa, T. et al., "Detection of Alcohol–Tolerant Hiochi Bacteria by PCR," *Applied and Environmental Microbiology*, 60(2):637–640 (1994).

Ness, F. et al., "Identification of Yeast Strains Using the Polymerase Chain Reaction," *J. Sci. Food Agric.*, 62:89–94 (1993).

Niepold, F. et al., "Application of the PCR technique to detect *Phytophthora infestans* in potato tubers and leaves," *Microbiol. Res.*, 150:379–385 (1995).

Niesters, H.G. et al., "Rapid, polymerase chain reaction–based identification assays for Candida species," *J. Clin. Microbiol.*, 31(4):904–910 (1993).

O'Gorman, D. et al., "Detection of *Leptosphaeria korrae* with the polymerase chain reaction and primers from the ribosomal internal transcribed spacers," *Canadian Journal of Botany*, 72:342–346 (1994).

Oda, Y. et al., "A Phylogenetic Analysis of Saccharomyces Species by the Sequence of 18S–28S rRNA Spacer Regions," *Yeast*, 13:1243–1250 (1997).

Omunyin, M.E. et al., "Use of Unique RNA Sequence–Specific Oligonucleotide Primers for RT–PCR to Detect and Differentiate Soybean Mosaic Virus Strains," *Plant Disease*, 80(10):1170–1174 (1996).

Paffetti, D. et al., "DNA fingerprinting by random amplified polymorphic DNA and restriction fragment length polymorphism is useful for yeast typing," *Research Microbiology*, 146:587–594 (1995).

Panchal, C.J. et al., "A Rapid, Simple and Reliable Method of Differentiating Brewing Yeast Strains Based on DNA Restriction Patterns," *Journal of the Institute of Brewing*, 93:325–327 (1987).

Pearson, B.M. et al., "Rapid identification of *Saccharomyces cerevisiae, Zygosaccharomyces bailii* and *Zygosaccharomyces rouxii*," *Int. J. Food Microbiol.*, 16:63–67 (1992).

Péros, J. et al., "Variation in Pathogenicity and Genetic Structure in the *Eutypa lata* Population of a Single Vineyard," *Ecology and Population Biology*, 87(8):799–806 (1997).

Prariyachatigul, C. et al., "Assessment of a PCR technique for the detection and identification of *Cryptococcus neoformans*," *J. Medical & Veterinary Mycology*, 34:251–258 (1996).

Prillinger, H. et al., "Phytopathogenic filamentous (Ashbya, Eremothecium) and dimorphic fungi (Holleya, Nematospora) with needle–shaped ascospores as new members within the Saccharomycetaceae," *Yeast*, 13(10):945–960 (1997).

Querol, A. et al., "A Comparative Study of Different Methods of Yeast Strain Characterization," *Systematic and Applied Microbiology*, 15:439–446 (1992).

Raeder et al., "Rapid Preparation of DNA from Filamentous Fungi," *Letters in Applied Microbiology*, 1:17–20 (1985).

Rand, K.H. et al., "Detection of candidemia by polymerase chain reaction," *Molecular and Cellular Probes*, 8:215–222 (1994).

Rehner, S.A. et al., "Nuclear ribosomal internal transcribed spacer phylogeny and host diversity in the coelomycete Phomopsis," *Can. J. Bot.*, 72:1666–1674 (1994).

Rodríguez, J.M. et al., "PCR Detection of the Lactocin S Structural Gene in Bacteriocin–Producing Lactobacilli from Meat," *Applied and Environmental Microbiology*, 61(7):2802–2805 (1995).

Rubini, A. et al., "Single step molecular characterization of morphologically similar black truffle species," *FEMS Microbiol. Lett.*, 164:7–12 (1998).

Schönian, G. et al., "Identification of clinical strains of *Candida albicans* by DNA fingerprinting with the polymerase chain reaction," *Mycoses*, 36:171–179 (1993).

Simon, L., In: *Methods and Molecular Biology, vol. 50: Species Diagnostics Protocols: PCR and Other Nucleic Acid Methods*, Edited by: J.P. Clapp, Humana Press Inc., Totowa, N.J., pp. 187–192 (1996).

Smart, C.D. et al., "Phytoplasma–Specific PCR Primers Based on Sequences of the 16S–23S rRNA Spacer Region," *Applied and Environmental Microbiology*, 62(8):2988–2993 (1996).

Sequence Similarity Search Results.

Sood, S.K. et al., "PCR–based detection of *Listeria monocytogenes* in dairy foods," *Current Science*, 71(6):449–456 (1996).

Stubbs, S. et al., "Differentiation of the spoilage yeast *Zygosaccharomyces bailii* from other Zygosaccharomyces species using 18S rDNA as target for a non-radioactive ligase detection reaction," Lett. Appl. Microbiol., 19:268–272 (1994).

Tsen, H. et al., "Possible Use of a Polymerase Chain Reaction Method for Specific Detection of Salmonella in Beef," *J. Fermentation and Bioengineering*, 77(2):137–143 (1994).

Tuchili, L.M. et al., "Detection of Salmonella DNA in Chicken Embryos and Environmental Samples by Polymerase Chain Reaction," *J. Vet. Med. Sci.*, 58(9):881–884 (1996).

Valente, P. et al., "PCR-amplified ITS length variation within the yeast genus Metschnilkowia," *J. Gen. Appl. Micorbiol.*, 43(3):179–181 (1997).

Vaughan–Martini, A. et al., "Differential killer sensitivity as a tool for fingerprinting wine–yeast strains of *Saccharomyces cerevisiae*," *J. Industrial Microbiology*, 17:124–127 (1996).

Vezinhet, F. et al., "Chromosomal DNA patterns and mitochondrial DNA polymorphism as tools for identification of enological strains of *Saccharomyces cerevisiae*," *Applied Microbiology and Biotechnology*, 32:568–571 (1990).

Vezinhet, F. et al., "Ecological Survey of Wine Yeast Strains by Molecular Methods of Identification," *American Journal of Enology and Viticulture*, 43(1):83–86 (1992).

Walsh, T.J. et al., "PCR and Single–Strand Conformational Polymorphism for Recognition of Medically Important Opportunistic Fungi," *J. Clinical Microbiology*, 3216–3220 (1995).

White, T.J. et al., "Amplification and direct sequencing of fungal ribosomal RNA genes for phylogenetics,"*PCR Protocols: : A Guide to Methods and Applications*, M. Innis, D.H. Gelfand et al., Eds., Academic Press, San Diego, CA pp. 315–322 (1990).

Williams, D.W. et al., "Identification of Candida species by PCR and restriction fragment length polymorphism analysis of intergenic spacer regions of ribosomal DNA," *J. Clin. Microbiol.*, 33(9):2476–2479 (1995).

Zhu, Q. et al., "Detection of *Salmonella typhi* by polymerase chain reaction," *J. Applied Bacteriology*, 80:244–251 (1996).

* cited by examiner

DETECTION OF FERMENTATION-RELATED MICROORGANISMS

FIELD OF THE INVENTION

The present invention relates to assays to detect fermentation-related microorganisms.

DESCRIPTION OF THE RELATED ART

In traditional winemaking, the indigenous yeasts ferment the grape must. Most modern winemakers, however, inoculate with a pure culture of a selected yeast strain to ensure a rapid, reliable and predictable fermentation. It is thought that indigenous yeasts are suppressed by the competitive effect of addition of a high-density monoculture, but some evidence suggests that indigenous yeast can still participate in the fermentation. A range of commercial yeasts with different winemaking characteristics is available, and a number of those yeast strains may be used in a single winery. Furthermore, unwanted microorganisms may be present which lead to spoilage. Therefore, there is a need for a rapid, simple and accurate method for identifying microorganisms in starter cultures and fermentations.

Past techniques for detecting and identifying fermentation-related microorganisms, especially yeast, include colony morphology, fermentation performance, sugar fermentation tests, tolerance to various stresses (e.g., ethanol tolerance) phenotypes with functional relevance (e.g., flocculation) nutritional requirements (e.g., oxygen), and resistance and sensitivity levels of cycloheximide. These methods, however, have numerous disadvantages, including lengthy analysis periods, inability to differentiate, e.g., different strains of yeast, and lack of reproducibility.

Recent developments in molecular biology and protein chemistry have provided new methods for identifying microorganisms, including DNA restriction fragment length polymorphisms, protein electrophoresis patterns and chromosome fingerprinting. Such techniques have been used for identifying fermentation-related microorganisms. See, for example, Casey et al., *Journal of the American Society of Brewing Chemists*, 48(3): 100–106, 1990; Degre et al., *American Journal of Enology and Viticulture*, 40(4): 309–315, 1989; Guillamon et al., *Systematic and Applied Microbiology*, 19:122–132, 1992; Hoeben et al., *Current Genetics*, 10:371–379, 1986, Mozina et al., *Letters in Applied Microbiology*, 24(4):311–315, 1997; Paffetti et al., *Research Microbiology*, 146:587–594, 1995; Panchal et al., *Journal of the Institute of Brewing*, 93:325–327, 1987; Querol et al., *Systematic and Applied Microbiology*, 15:439–446, 1992, Vezinhet et al., *Applied Microbiology and Biotechnology*, 32:568–571, 1990, and Vezinhet et al., *American Journal of Enology and Viticulture*, 43(1):83–86, 1992.

Polymerase chain reaction (PCR)-based techniques have also been used to detect fermentation-related microorganisms. See, for example, DeBarros Lopes et al., *Applied and Environmental Microbiology*, 62(12):4514–4520, 1996; Fell, *Molecular Marine Biology and Biotechnology*, 2(3): 174–180, 1993; Fell, *Journal of Industrial Microbiology*, 14(6):475–477, 1995; Ibeas et al., *Applied and Environmental Microbiology*, 62(3):998–1003, 1996; Lavallee et al., *American Journal of Enology and Viticulture*, 45(1):86–91, 1994; Lieckfeldt et al., *Journal of Basic Microbiology*, 33(6):413–425, 1993, and Ness et al., *J Sci. Food Agric.*, 62:89–94, 1993.

Ribosomal genes are suitable for use as molecular probe targets because of their high copy number. Non-transcribed and transcribed spacer sequences associated with ribosomal genes are usually poorly conserved and, thus, are advantageously used as target sequences for the detection of recent evolutionary divergence. Fungral rRNA genes are organized in units. Each unit encodes mature subunits of 18S, 5.8S, and 28S rRNA. The internal transcribed spacer (ITS) region lies between the 18S and 28S rRNA genes and contains two variable non-coding spacers (referred to as ITS1 and ITS2) and the 5.8S rRNA gene (White et al., 1990; In: *PCR Protocols*; Eds.: Innes et al pages 315–322). In addition, the transcriptional units are separated by non-transcribed spacer sequences (NTSs). The ITS and NTS sequences are particularly suitable for the detection of different fungal pathogens.

Kumeda et al. (*Applied and Environmental Microbiology*, 62(8):2947–2952, 1996) describes use of PCR to amplify ribosomal DNA internal transcribed spacers in order to differentiate species of Aspergillus Section Flavi. The ITSI-5.8S-ITS2 region was amplified using, universal primers, and the PCR product analyzed by the principle of single-strand conformation polymorphism. In addition, Gardes et al. (In: *Methods in Molecular Biology, Vol. 50:Species Diagnostics Protocols: PCR and Other Nucleic Acid Methods*, Ed. J. P. Clapp, Humana Press, Totowa, N.J., (1996) pp. 177–186) describes restriction fragment length polymorphism (RFLP) analysis of fungal ITS regions amplified by PCR.

The PCR amplification of fungal ITS has also been described using other than universal primers. These methods allow for more specificity in identifying classes of fungi, or particular species of fungi. Thus, Gardes and Bruns (*Molecular Ecology*, 2:113–118, 1993) identified ITS primers which allow differentiation of DNA from basidiomycetes against ascomycete DNA. Identification of specific species has been observed using PCR primers directed to unique sequences in the ITS1 and/or ITS2 regions of fungal pathogens. See, for example, Hamelin et al., *Applied and Environmental Microbiology*, 62(11):4026–4031, 1996, Mazzola et al., *PhytoPathology*, 86(4):354–360, 1996, O'Gorman et al., *Canadian Journal of Botany*, 72:342–346, 1994, and U.S. Pat. No. 5,585,238 to Ligon et al.

Of interest to the present application is the disclosure of PCT International Application US99/04251 based on U.S. application Ser. No. 09/037,990 which relates to oligonucleotide primers for the ITS of ribosomal RNA gene regions of fermentation-related microorganisms such as *Botrytis cinerea*, Penicillium, Brettanomyces/Dekkera, Saccharomyces, Hanseniaspora/Kloeckera, *Candida krusei/Issatchenkia orientalis*, *Pichia kluyveri*, *Pichia anomala/Candida pelliculosa*, *Debaryomyces carsonii*, and *Saccharomycodes ludwigii*. Also of interest to the present application is the disclosure of PCT International Application US98/25219 based on U.S. application Ser. No. 08/986, 727 which relates to oligonucleotide primers for the ITS of ribosomal RNA gene regions of fungal pathogens such as those that infect grape plants.

The present invention addresses the problem of detecting and identifying fermentation-related microorganisms by PCR-based techniques.

SUMMARY OF THE INVENTION

The present invention is directed to the identification of different fermentation-related microorganisms, particularly those involved in the production of wine. The present invention provides DNA sequences which exhibit variability between different fermentation-related microorganisms. In particular, the present invention identities regions of DNA sequence located in the internal transcribed spacer (ITS) of the ribosomal RNA gene regions of various fermentation-related microorganisms. Primers derived from the ITS can be used in polymerase chain reaction (PCR)-based and other diagnostic assays to determine the presence or absence of specific fermentation-related microorganisms, including those involved in the production of wine. The primers can also be used as molecular probes to detect the presence of target DNA.

Thus, in one aspect, the present invention provides an isolated double stranded nucleic acid of the full length ITS1 or ITS2 region of a fermentation-related microorganism. More particularly, the DNA sequence is selected from among Sequence ID NOS: 6 to 15 and their complementary sequences.

In another aspect, the present invention provides an oligonucleotide primer for identification of a fermentation-related microorganism, wherein the primer is a divergent portion of the ITS1 or ITS2 region of a fermentation-related microorganism. More particularly, the oligonucleotide primer is selected from among Sequence ID NOS: 16 to 24. Furthermore, the oligonucleotide primers may be selected from among sequences which contain at least 10 contiguous nucleotide bases from one of SEQ ID NOS: 16 to 24, primers which contain at least 10 contiguous nucleotide bases from one of SEQ ID NOS: 16 to 24 contiguous with 1 to 15 flanking, nucleotide bases in the 5' and/or 3' direction of SEQ ID NOS: 6 to 15, and primers of 10 nucleotide bases or longer which contain at least 5 contiguous nucleotide bases from one of SEQ ID NOS: 16 to 24 contiguous with from 1 to 15 flanking nucleotide bases in the 5' and/or 3' direction of SEQ ID NOS: 6 to 15. A pair of the foregoing oligonucleotide primers for use in the amplification-based detection of an ITS of a fermentation-related microorganism is also provided.

In yet another aspect, a method is provided for detection of a fermentation-related microorganism which comprises: (a) obtaining DNA from a fungal culture or colony isolated from a fermentation, or from an organism present in a fermentation beverage, (b) amplifying a part of the ITS of the fermentation-related microorganism using the DNA as a template in a polymerase chain reaction with the aforementioned oligonucleotide primers, and (c) detecting the amplified part of the ITS sequence to determine whether the fermentation-related microorganism is present.

In still another aspect, kits are provided which are useful in detecting fermentation-related microorganisms comprising one or more containers, at least one of which comprise an oligonucleotide primer or a pair of oligonucleotide primers according to the invention.

Brief Description of the Sequences in the Sequence Listing:

| | |
|---|---|
| SEQ ID NO: 1 | DNA sequence for the internal transcribed spacer of *Metschnikowia pulcherrima*. |
| SEQ ID NO: 2 | DNA sequence for the internal transcribed spacer of *Candidia stellata*. |
| SEQ ID NO: 3 | DNA sequence for the internal transcribed spacer of *Zygosaccharomyces bailii*. |
| SEQ ID NO: 4 | DNA sequence for the internal transcribed spacer of *Kluyveromyces thermotolerans*. |
| SEQ ID NO: 5 | DNA sequence for the internal transcribed spacer of *Torulaspora delbrueckii*. |
| SEQ ID NO: 6 | DNA sequence for the ITS1 of *Metschnikowia pulcherrima*. |
| SEQ ID NO: 7 | DNA sequence for the 1TS2 of *Metschnikowia pulcherrima*. |
| SEQ ID NO: 8 | DNA sequence for the ITS1 of *Candida stellata*. |

-continued

Brief Description of the Sequences in the Sequence Listing:

| | |
|---|---|
| SEQ ID NO: 9 | DNA sequence for the ITS2 of *Candida stellata*. |
| SEQ ID NO: 10 | DNA sequence for the ITS1 of *Zygosaccharomyces bailii*. |
| SEQ ID NO: 11 | DNA sequence for the ITS2 of *Zygosaccharomyces bailii*. |
| SEQ ID NO: 12 | DNA sequence for the ITS1 of *Kluyveromyces thermotolerans*. |
| SEQ ID NO: 13 | DNA sequence for the ITS2 of *Kluyveromyces thermotolerans*. |
| SEQ ID NO: 14 | DNA sequence for the ITS1 of *Torulaspora delbrueckii*. |
| SEQ ID NO: 15 | DNA sequence for the ITS2 of *Torulaspora delbrueckii*. |
| SEQ ID NO: 16 | Oligonucleotide Sequence MXL258. |
| SEQ ID NO: 17 | Oligonucleotide Sequence MXL268. |
| SEQ ID NO: 18 | Oligonucleotide Sequence CsF. |
| SEQ ID NO: 19 | Oligonucleotide Sequence CsR. |
| SEQ ID NO: 20 | Oligonucleotide Sequence QAZ165. |
| SEQ ID NO: 21 | Oligonucleotide Sequence QAZ622. |
| SEQ ID NO: 22 | Oligonucleotide Sequence GSZ450 |
| SEQ ID NO: 23 | Oligonucleotide Sequence TdF1 |
| SEQ ID NO: 24 | Oligonucleotide Sequence TdR1 |
| SEQ ID NO: 25 | Oligonucleotide Sequence ITS5. |
| SEQ ID NO: 26 | Oligonucleotide Sequence ITS4. |

DETAILED DESCRIPTION OF THE INVENTION

The present invention provides unique DNA sequences which are useful in identifying fermentation-related microorganisms. These unique DNA sequences can be used as primers in PCR-based analysis for the identification of fermentation-related microorganisms, or as molecular probes to detect the presence of DNA from fermentation-related microorganisms. The DNA sequences of the present invention include the internal transcribed spacer (ITS) of the ribosomal RNA gene regions of specific fermentation-related microorganisms, as well as primers that are derived from these regions which are capable of identifying the particular microorganism.

The DNA sequences of the invention are from the ITS of the ribosomal RNA gene region of fermentation-related microorganisms. However, the present invention is not limited to detecting the presence of the microorganisms in fermentation operations, i.e., the invention can be used to detect the presence of such microorganisms from any source. There is variability in the ITS DNA sequences from different microorganisms. The ITS sequences can be aligned and compared. Primers can be designed based on regions within the ITS regions that contain the greatest differences in sequence among the fermentation-related microorganisms. The sequences and primers based on these sequences can be used to identify specific microorganisms.

DNA sequences of particular interest include ITS DNA sequences from Metschnikowia sp., especially *Metschnikowia pulcherrima* ( anamorph *Candida pulcheirrima*); Zygosaccharomyces sp., especially *Zygosaccharomyces bailii*, Kluyveromyces sp., especially *Kluyveromyces thermotolerans* Candida sp., especially *Candida stellata* and Torulaspora sp.; especially *Torulaspora delbrueckii* (anamorph *Candida colliculosa*). The ITS DNA sequences, as well as primers of interest, are set forth in SEQUENCE ID NOS: 1–24. The sequences are useful in PCR-based identification of fermentation-related microorganisms.

Methods for use of the primer sequences of the invention in PCR analysis are well known in the art. For example, see U.S. Pat. Nos. 4,683,195; 4,683,202 and 5,585,238, the contents of all of which are hereby incorporated by reference.

The primer sequences of the invention can also be used as molecular probes to detect the presence of target DNA. The $T_m$ for the primers ranges from about 48–58° C. at 50 mM salt. The hybridization temperature is approximately 5–10° C. below the melting temperature. Thus, the primers are hybridized to target DNA typically at a temperature ranging from about 43–55° C. Final wash conditions generally range from about 45–55° C. at about 36 mM salt concentration. Specific hybridization as used herein means the use of a final high stringency wash in about 0.2×SSPE (salt concentration of about 36 mM) at a temperature appropriate for the particular primer. 1×SSPE contains 10 mM $NaH_2PO_4$, 180 mM NaCl, and 1 mM EDTA, at pH 7.4.

The ITS DNA sequences of the present invention can be cloned from fermentation-related microorganisms by methods known in the art. In general, the methods for the isolation of DNA from microorganism isolates are known. See, Raeder et al., *Letters in Applied Microbiology*, 2:17–20, 1985, Lee et al., *Fungal Genetics Newsletter*, 35:23–24, 1990; and Lee et al., In: *PCR Protocol: A Guide to Methods and Applications,* Innes et al. (Eds.); pages 282–287, 1990; the contents of all of which are hereby incorporated by reference.

Alternatively, the ITS regions of interest can be identified by PCR amplification. Primers to amplify the entire ITS region can be synthesized according to White et al. (1990, In *PCR Protocols;* Eds.: Innes et al., pages 315–322, the contents of which are hereby incorporated by reference).

The ITS sequences were determined and the sequences were compared to locate divergences which might be useful to test in PCR to distinguish the different fermentation-related microorganisms. The sequences of the ITS regions which were determined are shown as Sequence ID NOS: 1 to 5. The DNA sequences for the ITS1 and ITS2 regions are shown as Sequence ID NOS: 6 to 15. From the identification of divergences, numerous primers were synthesized tested in PCR-amplification. Purified microorganism DNA and DNA isolated from fermentation cultures and colonies were used as templates for PCR-amplification. Thus, pairs of diagnostic primers were identified, i.e, those which identified one particular fermentation-related microorganism species Preferred primer combinations are able to distinguish between the different microorganisms in, for example, fermentation cultures. Primer sequences are set forth in Sequence ID NOS: 16 to 24. Thus, while oligonucleotide primers selected from among Sequence ID NOS: 16 to 24 are preferred, primers may also be used which contain at least 10 contiguous nucleotide bases from one of SEQ ID NOS: 16 to 24. Additionally, primers may be used which contain at least 10 contiguous nucleotide bases from one of SEQ ID NOS: 16 to 24 contiguous with 1 to 15 flanking nucleotide bases in the 5' and/or 3' direction of corresponding SEQ ID NOS: 6 to 15, and primers of 10 nucleotide bases or longer which contain at least 5 contiguous nucleotide bases from one of SEQ ID NOS: 16 to 24 contiguous with from 1 to 15 flanking nucleotide bases in the 5' and/or 3' direction of corresponding SEQ ID NOS: 6 to 15.

The present invention provides numerous diagnostic primer combinations. The primers of the invention are designed based on sequence differences among the microorganism ITS regions. A minimum of one base pair difference between sequences can permit design of a discriminatory primer. In general, primers should have a theoretical melting temperature between about 55° C. to about 65° C. to achieve good sensitivity, and should be void of significant secondary structure and 3' overlaps between primer combinations. Primers are generally at least about 10 nucleotide bases, more preferably at least about 15 to about 20 nucleotide bases, The oligonucleotide primers of the present invention are particularly useful in detecting microorganisms involved in fermentations, in particular, microorganisms selected from among Metschnikowia sp., especially *Metschnikowia pulcherrima* (anamorph *Candida pulcherrima*); Zygosaccharomyces sp., especially *Zygosaccharomyces bailii;* Kluyveromyces sp., especially *Kluyveromyces thermotolerans;* Candida sp., especially *Candida stellata* and Torulaspora sp., especially *Torulaspora delbrueckii* (anamorph *Candida colliculosa*). However, the primers of the present invention can also be used to detect the presence of the foregoing microorganisms from any source.

The present invention also relates to the preparation of "kits" containing elements for detecting fermentation-related microorganisms. Such a kit may comprise a carrier to receive therein one or more containers, such as tubes or vials. Unlabeled or detectably labeled oligonucleotide primers may be contained in one or more of the containers. The oligonucleotide primers may be present in lyophilized form, or in an appropriate buffer. One or more enzymes or reagents for use in PCR reactions may be contained in one or more of the containers. The enzymes or reagents may be present alone or in admixture, and in lyophilized form or in appropriate buffers. The kit may also contain any other component necessary for carrying out the present invention, such as buffers, extraction agents, enzymes, pipettes, plates, nucleic acids, nucleoside triphosphates, filter paper, gel materials, transfer materials, and autoradiography supplies.

The examples below illustrate typical experimental protocols which can be used in the isolation of ITS sequences, the selection of suitable primer sequences, the testing of primers for selective and diagnostic efficacy, and the use of such primers to detect the presence of a fermentation-related microorganism. Such examples are provided by way of illustration and not by way of limitation.

EXAMPLE 1

Culture of Yeast and Fungal Isolates

Viable isolates of *Candida stellata, Kluyveromyces thermotolerans, Metschnikowia pulcherrima, Torulaspora delbrueckii, Zygosaccharomyces bailii, Brettanomycese bruxellensis, Candida parapsilosis, Candida tropicalis, Hanseniaspora uvarum, Pichia anomola, Saccharomyces cerevisiae, Zygosaccharomyces bisporus,* and *Zygosaccharomyces cidri* were obtained from the E & J Gallo Winery, the Gallo of Sonoma Winery, the American Type Culture Collection (ATCC) or the Centraalbureau voor Schimmelcultures, The Netherlands (see Table 1). Yeasts were grown on any of several media of choice.

EXAMPLE 2

Amplification and Sequencing of the Internal Transcribed Spacer (ITS) Regions

The internal transcribed spacer region was amplified from the different isolates directly from the yeast colony using ITS5 (5' -GGAAGTAAAAGTCGTAACAAGG-3', SEQ ID NO: 25) and ITS4 (5' -TCCTCCGCTTATTGATATGC-3'; SEQ ID NO: 26). A sterile pipette tip was used to scrape a small amount of colony off of the plate and deposited into a 200-μl microcentrifuge tube containing 5 μl each of Gene-Amp® 10×PCR Buffer (PE Applied Biosystems, Foster City, Calif.; part no. N808-0160), 0.2 mM each of dATP, dCTP, dGTP, and dTTP (GeneAmp® dNTPs; PE Applied Biosystems, Foster City, Calif., part no. N808-0007), approximately 25 pmole/μl each of ITS5 and ITS4, and 2.5 Units AmpliTaq® DNA polymerase (PE Applied Biosystems; part no. N808-0160). Reactions were run for 35 cycles of 30 s at 94° C., 40 s at 58° C., and 2 min at 72° C., followed by a final elongation step at 72° C. for 10 min, on a Perkin Elmer GeneAmp® PCR System 9700 (PE Applied Biosystems). PCR products were purified using QIAquick® PCR Purification Kits (Qiagen Inc Santa Clarita, Calif.) to remove any excess primers, nucleotides, and polymerases. Five microliters of the purified PCR products were run on a 1.2% agarose gel with 5 μl of pGEM-3Zf(+) double-stranded DNA Control Template (0.2 g/L, PE Applied Biosystems) to approximate concentrations. All products were sequenced using the primers ITS5 and ITS4 (see sequences above, White et al., 1990; In: *PCR Protocols;* Eds.: Innes et al. pp. 315–322). Sequencing was performed on an PE Applied Biosystems 377 Automated DNA Sequencer® using ABI PRISM™ dRhodamine Terminator Cycle Sequencing Ready Reaction Kits® (PE Applied Biosystems; part no. 403044). Cycle sequencing products were run over Centri-Sep® spin columns (Princeton Separations, Inc., Adelphia, N.J.) to remove excess primers, dye-labeled terminators, nucleotides, and polymerases before being run on the automated sequencer.

EXAMPLE 3

Selection of Species-Specific Primers

The ITS sequences of the *Metschnikowia* sp., especially *Metschnikowia pulcherrima* (anamorph *Candida pulcherrima*); Zygosaccharomyces sp., especially *Aygosaccharomyces bailii;* Kluyveromyces sp., especially *Kluyveromyces thermotolerans;* Candida sp., especially *Candida stellata* and Torulaspora sp., especially *Torulaspora delbrueckii* (anamorph *Candida colliculosa*) isolates were aligned and primers were designed using Oligo 5.0 (National Biosciences, Inc., Plymouth, Minn.) in regions of maximum sequence difference between the target species. (See Table 2)

EXAMPLE 4

Primer Synthesis

Primers were synthesized on an Applied Biosystems 394 DNA/RNA Synthesizer® using phosphoramidite chemistry.

EXAMPLE 5

Verification of Primer Specificity to Target Species

Different annealing temperatures were tested to determine the optimal temperature for PCR for individual primers. In cases with multiple species-specific primers, different primer combinations were used to determine the best primer combination and annealing temperature to amplify a single species-specific DNA fragment. Species-specific amplification products were produced from primers designed from the ITS region between the 18S and 28S ribosomal DNA subunits of each yeast species of interest.

Species-specific primers were tested against other yeast species to confirm their failure to amplify targets in those species. Specifically, the *Metschnikowia pulcherrima*-specific primers (SEQ ID NOs: 16 and 17) were tested in various combinations with and without primers ITS5 (SEQ ID NO: 25) and ITS4 (SEQ ID NO: 26) against the following species (*Candida stellata, Kluyveromyces thermotolerans, Torulaspora delbrueckii, Zygosaccharomyces bailii, Brettanomyces bruxellensis, Candida parapsilosis, Candida tropicalis, Hanseniaspora uvarum, Pichia anomala, Saccharomyces cerevisiae, Zygosaccharomyces bisporus,* and *Zygosaccharomyces cidri*) and did not amplify targets in those species.

Further, the *Candida stellata*-specific primers (SEQ ID NOs: 18 and 19) were tested in various combinations with and without primers ITS5 (SEQ ID NO: 25) and ITS4 (SEQ ID NO: 26) against the following species (*Kluyveromyces thermotolerans, Metschnikowia pulcherrima, Torulaspora delbrueckii, Zygosaccharomyces bailii, Brettanomyces bruxellensis, Candida parapsilosis, Candida tropicalis, Hanseniaspora uvarum, Pichia anomala, Saccharomyces cerevisiae, Zygosaccharomyces bisporus,* and *Zygosaccharomyces cidri*) and did not amplify targets in those species.

Further, the *Zygosaccharomyces bailii*-specific primers (SEQ ID NOs: 20and 21) were tested in various combinations with and without primers ITS4 (SEQ ID NO: 26) and ITS5 (SEQ ID NO: 25) against the following species (*Candida stellata, Kluyveromyces thermotolerans, Metschnikowia pulcherrima, Torulaspora delbrueckii, Brettanomyces bruxellensis, Candida parapsilosis, Candida tropicalis, Hanseniaspora uvarum, Pichia anomala, Saccharomyces cerevisiae, Zygosaccharomyces bisporus,* and *Zygosaccharomyces cidri*) and did not amplify targets in those species.

Further, the *Kluyveromyces thermotolerans*-specific primer (SEQ ID NO: 22) was tested with ITS5 (SEQ ID NO: 26) against the following species (*Candida stellata, Metschnikowia pulcherrima, Torulaspora delbrueckii, Zygosaccharomyces bailii, Brettanomyces bruxellensis, Candida parapsilosis, Candida tropicalis, Hanseniaspora uvarum, Pichia anomala, Saccharomyces cerevisiae, Zygosaccharomyces bisporus,* and *Zygosaccharomyces cidri*) and did not amplify targets in those species.

Finally, the *Torulaspora delbrueckii*-specific primers (SEQ ID NOs: 23 and 24) were tested in various combinations with and without primers (SEQ ID NO: 26) and ITS5 (SEQ ID NO: 24) against the following species (*Candida stellata, Kluyveromyces thermotolerans, Metschnikowia pulcherrima, Zygosaccharomyces bailii, Brettanomyces bruxellensis, Candida parapsilosis, Candida tropicalis, Hanseniaspora uvarum, Pichia anomala, Saccharomyces cerevisiae, Zygosaccharomyces bisporus,* and *Zygosaccharomyces cidri* ) and did not amplify targets in those species.

EXAMPLE 6

Utilization of ITS sequences as diagnostic probes to hybridize with target DNA

1. Put chosen concentration of DNA sample in 100 ul of TE, pH 7.0.
2. Add 0.1 volume of 3.0 M NaOH, vortex to mix and incubate at 65° C. for 20 min to destroy the RNA and denature the DNA.
3 Spin down condensation. Allow samples to cool to room temp. Neutralize by adding 1.0 volume [110 μl] of 2M ammonium acetate, pH 7.0, vortex to mix Spin down to remove solution off of cap. Refrigerate until slot blot apparatus is ready
4. Apply to 220 μl slot-blot apparatus according to manufacturer's protocol.

5. Label ITS sequence probe according to kit manufacturer's recommendation.
6. Prehybridize blots in 1.0% BSA, 1 mM EDTA, 0.5 M NaHPO$_4$, pH 7.2, 7.0% sodium dodecyl sulfate for a minimum of 2 hr prior to adding the probe, and then hybridize for 16 hr at 45° C. Initial washes consist of two 30-min washes in 1×SSPE/0.1% SDS at 50° C. Transfer blots to a plastic tray and wash in 1×SSPE for 1 hr, at 50° C. with shaking. The final wash should consist of 15 min at 50° C. in 0.2X SSPE.

While the invention has been described in detail and with reference to specific embodiments thereof, it will be apparent to one skilled in the art that various changes and modifications can be made therein without departing from the spirit and scope thereof

TABLE 1

Sources of test isolates

| Species name | ID number | Source |
|---|---|---|
| Candida stellata | CBS157 | CBS[1] |
| Candida stellata | CBS2649 | CBS |
| Candida stellata | GS056 | Gallo of Sonoma[2] |
| Candida stellata | GS111 | Gallo of Sonoma |
| Candida stellata | GS128 | Gallo of Sonoma |
| Candida stellata | GS174 | Gallo of Sonoma |
| Kluyveromyces thermotolerans | GS003 | Gallo of Sonoma |
| Kluyveromyces thermotolerans | GS104 | Gallo of Sonoma |
| Kluyveromyces thermotolerans | GS119 | Gallo of Sonoma |
| Kluyveromyces thermotolerans | GS127 | Gallo of Sonoma |
| Kluyveromyces thermotolerans | GS132 | Gallo of Sonoma |
| Kluyveromyces thermotolerans | GS137 | Gallo of Sonoma |
| Kluyveromyces thermotolerans | GS138 | Gallo of Sonoma |
| Kluyveromyces thermotolerans | GS166 | Gallo of Sonoma |
| Metschnikowia pulcherrima | GS002 | Gallo of Sonoma |
| Metschnikowia pulcherrima | GS011 | Gallo of Sonoma |
| Metschnikowia pulcherrima | GS018 | Gallo of Sonoma |
| Metschnikowia pulcherrima | GS024 | Gallo of Sonoma |
| Metschnikowia pulcherrima | GS030 | Gallo of Sonoma |
| Metschnikowia pulcherrima | GS043 | Gallo of Sonoma |
| Metschnikowia pulcherrima | GS055 | Gallo of Sonoma |
| Metschnikowia pulcherrima | GS066 | Gallo of Sonoma |
| Torulaspora delbrueckii | GS038 | Gallo of Sonoma |
| Torulaspora delbrueckii | NS1-3 | Gallo of Sonoma |
| Torulaspora delbrueckii | NS1-5 | Gallo of Sonoma |
| Torulaspora delbrueckii | NS1-9 | Gallo of Sonoma |
| Torulaspora delbrueckii | NS1-11 | Gallo of Sonoma |
| Torulaspora delbrueckii | NS1-16 | Gallo of Sonoma |
| Torulaspora delbrueckii | NS1-19 | Gallo of Sonoma |
| Zygosaccharomyces bailii | QA17 | E & J Gallo Winery[3] |
| Zygosaccharomyces bailii | QA30 | E & J Gallo Winery |
| Zygosaccharomyces bailii | QA31 | E & J Gallo Winery |
| Zygosaccharomyces bailii | QA48 | E & J Gallo Winery |
| Zygosaccharomyces bailii | QA57 | E & J Gallo Winery |
| Brettanomyces bruxellensis | Y153 | E & J Gallo Winery |
| Candida parapsilosis | QA45 | E & J Gallo Winery |
| Candida tropicalis | QA44 | E & J Gallo Winery |
| Hanseniaspora uvarum | GS014 | Gallo of Sonoma |

TABLE 1-continued

Sources of test isolates

| Species name | ID number | Source |
|---|---|---|
| Pinchia anomala | 34080 | ATCC[4] |
| Saccharomyces cerevisiae | GS084 | Gallo of Sonoma |
| Zygosaccharomyces bisporus | Y476 | Gallo of Sonoma |
| Zygosaccharomyces cidri | 36238 | ATCC |

[1]Centraalbureau voor Schimmelcultures, The Netherlands
[2]Gallo of Sonoma Winery, Healdsburg, CA, USA
[3]E & J Gallo Winery, Modesto, CA, USA
[4]American Type Culture Collection, Rockville, MD, USA

TABLE 2

| Target Organism | Primer Name | Primer Sequence |
|---|---|---|
| Metschnikowia pulcherrima | MXL 258 | 5'-AAGCAGGACCAAACCGGAGG-3' (SEQ ID NO: 16) |
| Metschnikowia pulcherrima | MXL 268 | 5'-TATTAGGCCGAAGCAGGACC-3' (SEQ ID NO: 17) |
| Candida stellata | CsF | 5'-TTTGCCAAAACCACTGTGAACA-3'(SEQ ID NO: 18) |
| Candida stellata | CsR | 5'-TTTAAAGATTGGGCGCCTTTC-3' (SEQ ID NO: 19) |
| Zygosaccharomyces bailii | QAZ 165 | 5'-TGGGAGGATGGGTTCGTC-3' (SEQ ID NO: 20) |
| Zygosaccharomyces bailii | QAZ 622 | 5'-GCTATCACTCACCCAATCTC-3' (SEQ ID NO: 21) |
| Kluyveromyces thermotolerans | QSZ 450 | 5'-CCTCAGTCAGCAACAGCC-3' (SEQ ID NO: 22) |
| Torulaspora delbrueckii | TdF1 | 5'-CTATATGAATGAAGTTAGAGGACGTCTAAAGAT-3' (SEQ ID NO: 23) |
| Torulaspora delbrueckii | TdR1 | 5'-GGAAGCACGCACAAGACGTATC-3' (SEQ ID NO: 24) |

We claim:

1. An isolated double stranded nucleic acid which consists of a member selected from the group consisting of SEQ ID NOS: 6 to 9 and 12 to 13 and its complementary sequence.

2. An isolated nucleic acid which specifically hybridizes with a nucleic acid selected from the group consisting of SEQ ID NOS: 6 to 9 and their complementary sequences.

3. An oligonucleotide sequence for identification of a fermentation-related microorganism, wherein said sequence is selected from the group consisting of SEQ ID NOS: 16 to 24.

4. An oligonucleotide primer which is a fragment of the sequences according to claim 3, and which specifically hybridizes to the ITS1 or ITS2 of *Metschnikowia pulcherrima; Zygosaccharomyces bailii; Kluyveromyces thermotolerans; Candida stellata* and *Torulaspora delbrueckii*.

5. An oligonucleotide primer for identification of a fermentation-related microorganism, wherein said primer specifically amplifies at least a portion of the ITS1 region of SEQ ID NOS: 6, 8, 10, 12 or 14 or at least a portion of the ITS2 region of SEQ ID NOS: 7, 9, 11, 13 or 15 or which specifically amplifies at least a portion of the ITS region of a fungal pathogen selected from the group consisting of *Metschnikowia pulcherrima; Zygosaccharomyces bailii; Kluyveromyces thermotolerans; Candida stellata* and *Torulaspora delbrueckii*, wherein said primer is selected from the group consisting of primers which contain at least 10 contiguous nucleotide bases from one of SEQ ID NOS: 16 to 24, primers which contain at least 10 contiguous nucleotide bases from one of SEQ ID NOS: 16 to 24 contiguous with 1 to 15 flanking nucleotide bases in the 5' and/or 3' direction of SEQ ID NOS: 6 to 15, and primers of 10 nucleotide bases or longer which contain at least 5 contiguous nucleotide bases from one of SEQ ID NOS: 16 to 24 continuous with from 1 to 15 flanking nucleotide bases in the 5' and/or 3' direction of SEQ ID NOS: 6 to 15.

6. A pair of oligonucleotide primers for use in the amplification-based detection of an internal transcribed spacer sequence of a fermentation-related microorganism, wherein said primers specifically amplify at least a portion of the ITS1 region of SEQ ID NOS: 6, 8, 10, 12 or 14 or at least a portion of the ITS2 region of SEQ ID NOS: 7, 9, 11, 13 or 15 or which specifically amplify at least a portion of the ITS region of a fungal pathogen selected from the consisting of *Metschnikowia pulcherrima; Zygosaccharomyces bailii; Kluyveromyces thermotolerans; Candida stellata* and *Torulaspora delbrueckii*, wherein the primers are selected from the group consisting of primers which contain at least 10 contiguous nucleotide bases from one of SEQ ID NOS: 16 to 24 primers which contain at least 10 contiguous nucleotide bases from one of SEQ ID NOS: 16 to 24 contiguous with 1 to 15 flanking nucleotide bases in the 5' and/or 3' direction of SEQ ID NOS: 6 to 15, and primers of 10 nucleotide bases or longer which contain at least 5 contiguous nucleotide bases from one of SEQ ID NOS: 16 to 24 contiguous with from 1 to 15 flanking nucleotide bases in the 5' and/or 3' direction of SEQ ID NOS: 6 to 15.

7. The pair of oligonucleotide primers according to claim 6 which comprises SEQ ID NO: 16 and SEQ ID NO: 17.

8. The pair of oligonucleotide primers according to claim 6 which comprises SEQ ID NO: 18 and SEQ ID NO: 19.

9. The pair of oligonucleotide primers according to claim 6 which comprises SEQ ID NO: 20 and SEQ ID NO: 21.

10. The pair of oligonucleotide primers according to claim 6 which comprises SEQ ID NO: 23 and SEQ ID NO: 24.

11. A method for detection of a fermentation-related microorganism comprising:
(a) obtaining DNA from a fungal culture or colony isolated from a fermentation, or from an organism present in a fermentation beverage;
(b) amplifying a part of the internal transcribed spacer sequence of said fermentation-related microorganism using said DNA as a template in a polymerase chain reaction with a pair of oligonucleotide primers according to claim 6; and
(c) detecting said amplified part of the internal transcribed spacer sequence to determine whether said fermentation-related microorganism is present.

12. The method according to claim 11, wherein said fermentation-related microorganism is selected from the group consisting of *Metschnikowia pulcherrima; Zygosaccharomyces bailii; Kluyveromyces thermotolerans; Candida stellata* and *Torulaspora delbrueckii*.

13. The method according to claim 12, wherein said fermentation culture or fermentation beverage is a wine fermentation culture or wine fermentation beverage.

14. The method according to claim 12, wherein the pair of oligonucleotide primers comprises SEQ ID NO: 16 and SEQ ID NO: 17.

15. The method according to claim 12, wherein the pair of oligonucleotide primers comprises SEQ ID NO: 18 and SEQ ID NO: 19.

16. The method according to claim 12, wherein the pair of oligonucleotide primers comprises SEQ ID NO: 20 and SEQ ID NO: 21.

17. The method according to claim 12, wherein the pair of oligonucleotide primers comprises SEQ ID NO: 23 and SEQ ID NO: 24.

18. A kit comprising a carrier to receive therein one or more containers, at least one of said containers comprising an oligonucleotide primer according to claim 5.

19. A kit comprising a carrier to receive therein one or more containers, at least one of said containers comprising a pair of oligonucleotide primers according to claim 6.

20. The kit according to claim 19 comprising at least five pairs of oligonucleotide primers according to claim 6 wherein each pair specifically amplifies at least a portion of the ITS region of a different member selected from the group consisting of *Metschnikowia pulcherrima; Zygosaccharomyces bailii; Kluyveromyces thermotolerans; Candida stellata* and *Torulaspora delbrueckii*.

21. The method according to claim 12 comprising detecting the presence or absence of each member selected from the group consisting of *Metschnikowia pulcherrima; Zygosaccharomyces bailii; Kluyveromyces thermotolerans; Candida stellata* and *Torulaspora delbrueckii*.

* * * * *

UNITED STATES PATENT AND TRADEMARK OFFICE
CERTIFICATE OF CORRECTION

PATENT NO. : 6,287,779 B1
DATED : September 11, 2001
INVENTOR(S) : Engel et al.

It is certified that error appears in the above-identified patent and that said Letters Patent is hereby corrected as shown below:

Title page,
Item [56], OTHER PUBLICATIONS, First Cited Reference, please delete "htlm" and insert -- html -- in its place.
"GenBank Accerssion No. L47116", after "No. L47116," please insert -- " -- and after "5' end", please insert -- " --.

Column 2,
Line 10, after "Eds.: Innes et," please delete "al" and insert -- al. -- in its place.
Line 17, after "Second Flavi. The," please delete "ITSI" and insert
-- ITS1 -- in its place.
Line 18, after "was amplified," please delete "using," and insert -- using -- in its place.
Line 28, after "et al.," please delete "PhytoPathology" and insert
-- Phytopathology -- in its place.
Lines 47-48, after "*cinerea*," please delete "Penicillium, Brettanomyces/Dekkera, Saccharomyces," and insert -- *Penicillium, Brettanomyces/Dekkera, Saccharomyces,* -- in its place.
Line 53, after "tion," please delete "US98/25219," and insert -- US98/25210 -- in its place.
Line 67, after "the present invention," please delete "identities" and insert
-- identifies -- in its place.

Column 4,
Line 57, after "*Candida*," please delete "*pulcheirrima*" and insert -- *pulcherrima* -- in its place.
Line 59, please delete "*bailii*," and insert -- *bailii;* -- in its place.
Lines 59-60, after "*Kluyveromyces*," please delete "*thermotolerans*" and insert
-- *thermotolerans;* -- in its place.
Line 61, after "*Torulaspora*," please delete "sp.;" and insert -- sp. -- in its place.

Column 5,
Line 40, after "primers were," please delete "synthesized tested" and insert
-- synthesized and tested -- in its place.
Line 45, after "microorganism," please delete "species" and insert
-- species. -- in its place.

Column 6,
Line 6, after "otide," please delete "bases," and insert -- bases. -- in its place.
Line 49, after "*bailii*," please delete "*Brettanomycese*" and insert
-- *Brettanomyces* -- in its place.

UNITED STATES PATENT AND TRADEMARK OFFICE
CERTIFICATE OF CORRECTION

PATENT NO.    : 6,287,779 B1
DATED         : September 11, 2001
INVENTOR(S)   : Engel et al.

It is certified that error appears in the above-identified patent and that said Letters Patent is hereby corrected as shown below:

Column 10,
Lines 29-30, within the Table Column entitled "Primer Name" please delete "(SEQ ID NO: 17)" and insert -- (SEQ ID NO: 17) -- within the Table Column entitled "Primer Sequence" instead.
Lines 32-33, within the Table Column entitled "Target Organism" please delete "3' (SEQ ID NO: 18)" and insert -- 3' (SEQ ID NO: 18) -- within the Table Column entitled "Primer Sequence" instead.

Column 25,
Lines 44-45, after "selected from," please delete "the consisting" and insert -- the group consisting -- in its place.
Line 50, after "NOS: 16 to," please delete "24" and insert -- 24, -- in its place.

Signed and Sealed this

Twenty-second Day of July, 2003

JAMES E. ROGAN
*Director of the United States Patent and Trademark Office*

SEQUENCE LISTING

<160> NUMBER OF SEQ ID NOS: 26

<210> SEQ ID NO 1
<211> LENGTH: 344
<212> TYPE: DNA
<213> ORGANISM: Metschnikowia pulcherrima
<220> FEATURE:
<221> NAME/KEY: misc_feature
<222> LOCATION: (24)

```
<223> OTHER INFORMATION: At position 24, Y = C or T
<220> FEATURE:
<221> NAME/KEY: misc_feature
<222> LOCATION: (56)
<223> OTHER INFORMATION: At position 56, D = A, G, or T
<220> FEATURE:
<221> NAME/KEY: misc_feature
<222> LOCATION: (58)
<223> OTHER INFORMATION: At position 58, W = A or T
<220> FEATURE:
<221> NAME/KEY: misc_feature
<222> LOCATION: (60)
<223> OTHER INFORMATION: At position 60, R = A or G
<220> FEATURE:
<221> NAME/KEY: misc_feature
<222> LOCATION: (61)
<223> OTHER INFORMATION: At position 61, Y = C or T
<220> FEATURE:
<221> NAME/KEY: misc_feature
<222> LOCATION: (70)
<223> OTHER INFORMATION: At position 70, M = A or C
<220> FEATURE:
<221> NAME/KEY: misc_feature
<222> LOCATION: (74)
<223> OTHER INFORMATION: At position 74, Y = C or T
<220> FEATURE:
<221> NAME/KEY: misc_feature
<222> LOCATION: (76)
<223> OTHER INFORMATION: At position 76, R = A or G
<220> FEATURE:
<221> NAME/KEY: misc_feature
<222> LOCATION: (100)
<223> OTHER INFORMATION: At position 100, N = A, G, C, or T
<220> FEATURE:
<221> NAME/KEY: misc_feature
<222> LOCATION: (108)
<223> OTHER INFORMATION: At position 108, Y = C or T
<220> FEATURE:
<221> NAME/KEY: misc_feature
<222> LOCATION: (109)
<223> OTHER INFORMATION: At position 109, W = A or T
<220> FEATURE:
<221> NAME/KEY: misc_feature
<222> LOCATION: (110)
<223> OTHER INFORMATION: At position 110, Y = C or T
<220> FEATURE:
<221> NAME/KEY: misc_feature
<222> LOCATION: (111)
<223> OTHER INFORMATION: At position 111, W = A or T
<220> FEATURE:
<221> NAME/KEY: misc_feature
<222> LOCATION: (112)
<223> OTHER INFORMATION: At position 112, W = A or T
<220> FEATURE:
<221> NAME/KEY: misc_feature
<222> LOCATION: (114)
<223> OTHER INFORMATION: At position 114, H = A, C, or T
<220> FEATURE:
<221> NAME/KEY: misc_feature
<222> LOCATION: (115)
<223> OTHER INFORMATION: At position 115, M = A or C
<220> FEATURE:
<221> NAME/KEY: misc_feature
<222> LOCATION: (341)
<223> OTHER INFORMATION: At position 341, K = G or T
<220> FEATURE:
<221> NAME/KEY: misc_feature
<222> LOCATION: (342)
<223> OTHER INFORMATION: At position 342, Y = C or T

<400> SEQUENCE: 1
ggaagtaaaa gtcgtaacaa ggtytccgta ggtgaacctg cggaaggatc attaadawtr    60
ytattacacm cttytrggca caaactctaa atcttaaccn tcaataaywy wwthmaaaaa   120
ctttcaacaa cggatctctt ggttctcgca tcgatgaaga acgcagcgaa ttgcgatacg   180
taatatgact tgcagacgtg aatcattgaa tctttgaacg cacattgcgc cccggggtat   240
```

```
tccccagggc atgcgtgggt gagcgatatt tactctcaaa cctccggttt ggtcctgctt    300
cggcctaata tcaacggcgc tagaataagt tttagcccca kyct                    344
```

<210> SEQ ID NO 2
<211> LENGTH: 372
<212> TYPE: DNA
<213> ORGANISM: Candida stellata

<400> SEQUENCE: 2

```
ctgaaggctt tttgccaaaa ccactgtgaa cagcttagac ttcggtcttt gcaattgctt     60
gggtgtcgaa aggcgcccaa tctttaaaac ttttatattt gttctgaaac aatgaaaatt    120
taaaactttc aacaacggat ctcttggttc tcgtatcgat gaagaacgca gcaaagcgcg    180
ataggtaatg cgaattgcag acgtgagtca ttgaattttt gaacgcatat tgcgctatta    240
gtttgtctaa tagcatgctt gttggagtga taatcttcct ctcaaccatt tttggtatga    300
ggtcttgctc cttttaggag ttaaaatcat ggaagtgcac acgttaatta actctgtgca    360
gttatacact tt                                                       372
```

<210> SEQ ID NO 3
<211> LENGTH: 697
<212> TYPE: DNA
<213> ORGANISM: Zygosaccharomyces bailii

<400> SEQUENCE: 3

```
tagaacaatt tctcgattga ctatctggac cagttgtgtt ctttctgttt tttttaaggc     60
ctgcgcttaa ttgcgcggtc tagagcggag ggagttaagc atagttgctt tggctttcaa    120
tttacacaca gtggagtttc tacttttttt attcttcttt gggaggatgg gttcgtcccg    180
cttccagagg taaacacaaa caattttttt tattttattt tattttatta ttataataat    240
aataatacag tcaaaacgaa tactaaaaca aaaatattc aaaactttca acaacggatc    300
tcttggttct cgcatcgatg aagaacgcag cgaaatgcga tacgtaatgt gaattgcaga    360
attccgtgaa tcatcgaatc tttgaacgca cattgcgccc cttggtattc caggggggcat    420 gcctgtttga gcgtcatttc cttctcaaac attcgtgttt ggtagtgagt gatactctgt    480
tttattattt gggttaactt gaaattgcaa gccttttggg gacgcgtgtg ggtgagtttt    540
aggcggaaac gtcttgctct cctctttcct aaccaaatgt cgtattaggt tttaccgact    600
ccgacagacg ggactaggag attgggtgag tgatagcaat atcgagctct gcctaatttt    660
ttttttgcgc gccttgggca aacaatactc tcaaagt                            697
```

<210> SEQ ID NO 4
<211> LENGTH: 588
<212> TYPE: DNA
<213> ORGANISM: Kluyveromyces thermotolerans
<220> FEATURE:
<221> NAME/KEY: misc_feature
<222> LOCATION: (38)
<223> OTHER INFORMATION: At position 38, N = A, G, C or T
<220> FEATURE:
<221> NAME/KEY: misc_feature
<222> LOCATION: (530)
<223> OTHER INFORMATION: At position 530, N = A, G, C, or T

<400> SEQUENCE: 4

```
aagaattttg ttagagcagc cgggaaagtt cagaagcntg cgcttgattg cgcggccgat     60
gatgctttct gttaacgact gtctctctac acacacactg tggagtaatt tattttacaa    120
```

-continued

```
cgcttcttct ttgggctttta cggcccaagg gttacaaaca caaacaacta ttgtattta      180 aacattgtca attatttttc attttagaaa aaaatatt  aaaactttca acaacggatc      240
tcttggttct cgcatcgatg aagaacgcag cgaaatgcga taagtattgt gaattgcaga     300
tattcgtgaa tcatcgaatc tttgaacgca cattgcgccc tctggtattc caggggcat    360 gcctgttga gcgtcatttc cttctcaaac cctcgggttt ggtagtgagt ggtactcttt    420
ctgggttaac ttgaaaatgc tggccatctg gctgttgctg actgaggttt tagtccagtc    480
cgctgatact ctgcgtatta ggttttacca actcgtagtg cgttagtan cgttttaaa     540 ggctttact gaaagtacag acagtctggc aaacagtatt cataaagt                588
```

<210> SEQ ID NO 5
<211> LENGTH: 710
<212> TYPE: DNA
<213> ORGANISM: Torulaspora delbrueckii

<400> SEQUENCE: 5

```
gagaaatcta tatgaatgaa gttagaggac gtctaaagat actgtaagag aggatcaggt      60
tcaagaccag cgcttaattg cgcggttgcg gcttggttcg ccttttgcgg aacatgtctt    120
ttctcgttgt taactctact tcaacttcta caacactgtg gagttttcta cacaactttt   180
cttctttggg aagatacgtc ttgtgcgtgc ttcccagagg tgacaaacac aaacaactt   240 ttattattat aaaccagtca aaccaattt cgttatgaaa ttaaaaatat ttaaaacttt     300
caacaacgga tctcttggtt ctcgcatcga tgaagaacgc agcgaaatgc gatacgtaat    360
gtgaattgca gaattccgtg aatcatcgaa tctttgaacg cacattgcgc ccttggtat   420 tccaggggc atgcctgttt gagcgtcatt tccttctcaa acaatcatgt ttggtagtga    480
gtgatactct gtcaagggtt aacttgaaat tgctagcctg ttatttggtt gtgattttgc   540
tggcttggat gactttgtcc agtctagcta ataccgaatt gtcgtattag gtttaccaa    600 cttcggcaga ctgtgtgttg gctcgggcgc tttaaagact ttgtcgtaaa cgatttatcg   660
tttgtttgag cttttcgcat acgcaatccg gcgaacaata ctctcaaagt               710
```

<210> SEQ ID NO 6
<211> LENGTH: 63
<212> TYPE: DNA
<213> ORGANISM: Metschnikowia pulcherrima
<220> FEATURE:
<221> NAME/KEY: misc_feature
<222> LOCATION: (2)
<223> OTHER INFORMATION: At position 2, D= A, G, or T
<220> FEATURE:
<221> NAME/KEY: misc_feature
<222> LOCATION: (4)
<223> OTHER INFORMATION: At position 4, W = A or T
<220> FEATURE:
<221> NAME/KEY: misc_feature
<222> LOCATION: (6)
<223> OTHER INFORMATION: At position 6, R = A or G
<220> FEATURE:
<221> NAME/KEY: misc_feature
<222> LOCATION: (7)
<223> OTHER INFORMATION: At position 7, Y = C or T
<220> FEATURE:
<221> NAME/KEY: misc_feature
<222> LOCATION: (16)
<223> OTHER INFORMATION: At position 16, M = A or C
<220> FEATURE:
<221> NAME/KEY: misc_feature
<222> LOCATION: (20)
<223> OTHER INFORMATION: At position 20, Y = C or T
<220> FEATURE:
<221> NAME/KEY: misc_feature
<222> LOCATION: (22)
<223> OTHER INFORMATION: At position 22, R = A or G
<220> FEATURE:
<221> NAME/KEY: misc_feature
<222> LOCATION: (46)
<223> OTHER INFORMATION: At position 46, N = A, G, C, or T
<220> FEATURE:
<221> NAME/KEY: misc_feature
<222> LOCATION: (54)
<223> OTHER INFORMATION: At position 54, Y = C or T
<220> FEATURE:
<221> NAME/KEY: misc_feature
<222> LOCATION: (55)
<223> OTHER INFORMATION: At position 55, W = A or T
<220> FEATURE:
<221> NAME/KEY: misc_feature
<222> LOCATION: (56)
<223> OTHER INFORMATION: At position 56, Y = C or T
<220> FEATURE:
<221> NAME/KEY: misc_feature
<222> LOCATION: (57)
<223> OTHER INFORMATION: At position 57, W = A or T
<220> FEATURE:
<221> NAME/KEY: misc_feature
<222> LOCATION: (58)
<223> OTHER INFORMATION: At position 58, W = A or T
<220> FEATURE:
<221> NAME/KEY: misc_feature
<222> LOCATION: (60)
<223> OTHER INFORMATION: At position 60, H = A, C, or T
<220> FEATURE:
<221> NAME/KEY: misc_feature
<222> LOCATION: (61)
<223> OTHER INFORMATION: At position 61, M = A or C

<400> SEQUENCE: 6
adawtrytat tacacmctty trggcacaaa ctctaaatct taaccntcaa taaywywwth      60 maa                                                                   63

<210> SEQ ID NO 7
<211> LENGTH: 73
<212> TYPE: DNA
<213> ORGANISM: Metschnikowia pulcherrima
<220> FEATURE:
<221> NAME/KEY: misc_feature
<222> LOCATION: (70)
<223> OTHER INFORMATION: At position 70, K = G or T
<220> FEATURE:
<221> NAME/KEY: misc_feature
<222> LOCATION: (71)
<223> OTHER INFORMATION: At position 71, Y = C or T

<400> SEQUENCE: 7
actctcaaac ctccggtttg gtcctgcttc ggcctaatat caacggcgct agaataagtt      60
ttagccccak yct                                                        73

<210> SEQ ID NO 8
<211> LENGTH: 122
<212> TYPE: DNA
<213> ORGANISM: Candida stellata

<400> SEQUENCE: 8
ctgaaggctt tttgccaaaa ccactgtgaa cagcttagac ttcggtcttt gcaattgctt     60
gggtgtcgaa aggcgcccaa tctttaaaac ttttatattt gttctgaaac aatgaaaatt    120
ta                                                                   122

<210> SEQ ID NO 9
<211> LENGTH: 89
<212> TYPE: DNA

<213> ORGANISM: Candida stellata

<400> SEQUENCE: 9

| aaccattttt ggtatgaggt cttgctcctt ttaggagtta aaatcatgga agtgcacacg | 60 |
| ttaattaact ctgtgcagtt atacacttt | 89 |

<210> SEQ ID NO 10
<211> LENGTH: 281
<212> TYPE: DNA
<213> ORGANISM: Zygosaccharomyces bailii

<400> SEQUENCE: 10

| tagaacaatt tctcgattga ctatctggac cagttgtgtt ctttctgttt tttttaaggc | 60 |
| ctgcgcttaa ttgcgcggtc tagagcggag ggagttaagc atagttgctt tggctttcaa | 120 |
| tttacacaca gtggagtttc tactttttt attcttcttt gggaggatgg gttcgtcccg | 180 |
| cttccagagg taaacacaaa caattttttt tattttattt tatttatta ttataataat | 240 |
| aataatacag tcaaaacgaa tactaaaaca aaaatattc a | 281 |

<210> SEQ ID NO 11
<211> LENGTH: 258
<212> TYPE: DNA
<213> ORGANISM: Zygosaccharomyces bailii

<400> SEQUENCE: 11

| ccttctcaaa cattcgtgtt tggtagtgag tgatactctg ttttattatt tgggttaact | 60 |
| tgaaattgca agccttttgg ggacgcgtgt gggtgagttt taggcggaaa cgtcttgctc | 120 |
| tcctctttcc taaccaaatg tcgtattagg ttttaccgac tccgacagac gggactagga | 180 |
| gattgggtga gtgatagcaa tatcgagctc tgcctaattt tttttttgcg cgccttgggc | 240 |
| aaacaatact ctcaaagt | 258 |

<210> SEQ ID NO 12
<211> LENGTH: 221
<212> TYPE: DNA
<213> ORGANISM: Kluyveromyces thermotolerans
<220> FEATURE:
<221> NAME/KEY: misc_feature
<222> LOCATION: (38)
<223> OTHER INFORMATION: At position 38, N = A, G, C, or T

<400> SEQUENCE: 12

| aagaattttg ttagagcagc cgggaaagtt cagaagcntg cgcttgattg cgcggccgat | 60 |
| gatgctttct gttaacgact gtctctctac acacacactg tggagtaatt tattttacaa | 120 |
| cgcttcttct ttgggcttta cggcccaagg gttacaaaca caaacaacta ttgtattta | 180 |
| aacattgtca attattttc attttagaaa aaaaatattt a | 221 |

<210> SEQ ID NO 13
<211> LENGTH: 209
<212> TYPE: DNA
<213> ORGANISM: Kluyveromyces thermotolerans
<220> FEATURE:
<221> NAME/KEY: misc_feature
<222> LOCATION: (151)
<223> OTHER INFORMATION: At position 151, N = A, G, C or T

<400> SEQUENCE: 13

| ccttctcaaa ccctcgggtt tggtagtgag tggtactctt tctgggttaa cttgaaaatg | 60 |
| ctggccatct ggctgttgct gactgaggtt ttagtccagt ccgctgatac tctgcgtatt | 120 |

```
aggttttacc aactcgtagt ggcgttagta ngcgttttaa aggcttttac tgaaagtaca      180
gacagtctgg caaacagtat tcataaagt                                        209
```

<210> SEQ ID NO 14
<211> LENGTH: 293
<212> TYPE: DNA
<213> ORGANISM: Torulaspora delbrueckii

<400> SEQUENCE: 14

```
gagaaatcta tatgaatgaa gttagaggac gtctaaagat actgtaagag aggatcaggt       60
tcaagaccag cgcttaattg cgcggttgcg gcttggttcg ccttttgcgg aacatgtctt      120
ttctcgttgt taactctact tcaacttcta caacactgtg gagttttcta cacaactttt     180
cttctttggg aagatacgtc ttgtgcgtgc ttcccagagg tgacaaacac aaacaacttt     240
ttattattat aaaccagtca aaaccaattt cgttatgaaa ttaaaaatat tta            293
```

<210> SEQ ID NO 15
<211> LENGTH: 259
<212> TYPE: DNA
<213> ORGANISM: Torulaspora delbrueckii

<400> SEQUENCE: 15

```
ccttctcaaa caatcatgtt tggtagtgag tgatactctg tcaagggtta acttgaaatt      60
gctagcctgt tatttggttg tgattttgct ggcttggatg actttgtcca gtctagctaa    120
taccgaattg tcgtattagg ttttaccaac ttcggcagac tgtgtgttgg ctcgggcgct    180
ttaaagactt tgtcgtaaac gatttatcgt ttgtttgagc ttttcgcata cgcaatccgg    240
cgaacaatac tctcaaagt                                                  259
```

<210> SEQ ID NO 16
<211> LENGTH: 20
<212> TYPE: DNA
<213> ORGANISM: Oligonucleotide MXL258

<400> SEQUENCE: 16

```
aagcaggacc aaaccggagg                                                   20
```

<210> SEQ ID NO 17
<211> LENGTH: 20
<212> TYPE: DNA
<213> ORGANISM: Oligonucleotide MXL 268

<400> SEQUENCE: 17

```
tattaggccg aagcaggacc                                                   20
```

<210> SEQ ID NO 18
<211> LENGTH: 22
<212> TYPE: DNA
<213> ORGANISM: Oligonucleotide CsF

<400> SEQUENCE: 18

```
tttgccaaaa ccactgtgaa ca                                                22
```

<210> SEQ ID NO 19
<211> LENGTH: 21
<212> TYPE: DNA
<213> ORGANISM: Oligonucleotide CsR

<400> SEQUENCE: 19

```
tttaaagatt gggcgccttt c                                              21

<210> SEQ ID NO 20
<211> LENGTH: 18
<212> TYPE: DNA
<213> ORGANISM: Oligonucleotide QAZ165

<400> SEQUENCE: 20
tgggaggatg ggttcgtc                                                  18

<210> SEQ ID NO 21
<211> LENGTH: 21
<212> TYPE: DNA
<213> ORGANISM: Oligonucleotide QAZ622

<400> SEQUENCE: 21
gctatcactc acccaatctc c                                              21

<210> SEQ ID NO 22
<211> LENGTH: 19
<212> TYPE: DNA
<213> ORGANISM: Oligonucleotide GSZ450

<400> SEQUENCE: 22
acctcagtca gcaacagcc                                                 19

<210> SEQ ID NO 23
<211> LENGTH: 33
<212> TYPE: DNA
<213> ORGANISM: Oligonucleotide TdF1

<400> SEQUENCE: 23
ctatatgaat gaagttagag gacgtctaaa gat                                 33

<210> SEQ ID NO 24
<211> LENGTH: 22
<212> TYPE: DNA
<213> ORGANISM: Oligonucleotide TdR1

<400> SEQUENCE: 24
ggaagcacgc acaagacgta tc                                             22

<210> SEQ ID NO 25
<211> LENGTH: 22
<212> TYPE: DNA
<213> ORGANISM: Oligonucleotide ITS5

<400> SEQUENCE: 25
ggaagtaaaa gtcgtaacaa gg                                             22

<210> SEQ ID NO 26
<211> LENGTH: 20
<212> TYPE: DNA
<213> ORGANISM: Oligonucleotide ITS4
<220> FEATURE:

<400> SEQUENCE: 26
tcctccgctt attgatatgc                                                20
```